United States Patent
Hsu

(10) Patent No.: US 11,459,288 B2
(45) Date of Patent: Oct. 4, 2022

(54) PROCESS FOR PREPARING AZELAIC ACID

(71) Applicant: CORUM INC., Taipei (TW)

(72) Inventor: Nai-Hsuan Hsu, Taipei (TW)

(73) Assignee: CORUM INC., Taipei (TW)

( * ) Notice: Subject to any disclaimer, the term of this patent is extended or adjusted under 35 U.S.C. 154(b) by 147 days.

(21) Appl. No.: 16/933,212

(22) Filed: Jul. 20, 2020

(65) Prior Publication Data

US 2021/0047257 A1 Feb. 18, 2021

Related U.S. Application Data

(60) Provisional application No. 62/885,342, filed on Aug. 12, 2019.

(51) Int. Cl.
  *C07C 51/38* (2006.01)
  *C07C 55/18* (2006.01)

(52) U.S. Cl.
  CPC .............. *C07C 51/38* (2013.01); *C07C 55/18* (2013.01)

(58) Field of Classification Search
  CPC ................................. C07C 51/38; C07C 55/18
  USPC ......................................................... 562/512
  See application file for complete search history.

(56) References Cited

U.S. PATENT DOCUMENTS

2019/0194115 A1* 6/2019 Thamatam ............ C07C 67/343

FOREIGN PATENT DOCUMENTS

| CN | 108238913 | * | 7/2018 |
|---|---|---|---|
| CN | 108238913 A | | 7/2018 |
| JP | 59007162 B | * | 1/1974 |

* cited by examiner

*Primary Examiner* — Ana Z Muresan
(74) *Attorney, Agent, or Firm* — WPAT, PC

(57) ABSTRACT

A process for preparing azelaic acid is disclosed. In particular, the process for preparing azelaic acid is an ozone free process. The process for preparing azelaic acid comprises a step of decarboxylation of tetra-carboxylic acid in the presence of a organic sulfonic acid.

6 Claims, 2 Drawing Sheets

RCH$_2$CN
R = H or electron withdrawing groups (EWGs)
nitrile alpha carboanions

+

X is a leaving group which comprises a halogen or a alkyl sulfonate

R$_1$ = H atom or C1~C4 groups (2)     or     (3)

PROCESS FOR PREPARING AZELAIC ACID

TECHNICAL FIELD OF THE INVENTION

The invention relates to a process for preparing azelaic acid. In particular, the process for preparing azelaic acid is an ozone free process.

BACKGROUND OF THE INVENTION

Chemically, azelaic acid is an aliphatic dicarboxylic acid that has nine carbon numbers.

Industrially, azelaic acid is produced by ozonolysis of oleic acid at the carbon-carbon double bond to form azelaic acid and pelargonic acid that is a main byproduct. However, the oleic acid purity is usually 70%, as a result, the pelargonic acid and other impurities need to be further removed by complicated purifications for obtaining azelaic acid with purity more than 98%.

In cosmetic and pharmaceutical field, azelaic acid is a component of personal care products and in the treatment of rosacea and acne.

Based on the aforementioned description, there is a continuing need to develop a process that can prepare azelaic acid with high purity.

SUMMARY OF THE INVENTION

In one aspect of the invention, a first process for preparing azelaic acid is disclosed in scheme 1 as shown in FIG. 1. The process comprises following steps. The steps include: react a carbanion with a compound has a formula of (1) to form an intermediate having a formula of (2). Perform alcoholysis of the intermediate to form an alkyl di-ester; and hydrolyze the alkyl di-ester in the presence of bases to obtain a alkyl di-acid salt; and follow by acidifying the alkyl di-acid salt to obtain azelaic acid; or hydrolyze the alkyl di-ester in the presence of acids to obtain azelaic acid. The azelaic acid prepared according to the process does not contain fatty acids, such as pelargonic acid.

The compound has a formula of (1) comprises a pentane has two leaving groups bound to 1 and 5 carbon.

In one embodiment, the carbanions are generated by adding a deprotonating reagent to a compound has alpha hydrogen atoms adjacent to nitrile groups or electron-withdrawing groups in inert solvents.

The compound has alpha hydrogen atoms adjacent to nitrile groups comprises acetonitrile, cyanoacetic acid, alkyl cyanoacetate or malonitrile.

The compound has alpha hydrogen atoms adjacent to electron-withdrawing groups comprises diethyl malonate or di tert butyl malonate.

The deprotonating reagent comprises strong bases or weak bases.

The strong bases comprise metal amide, such as sodium amide or potassium amide, or metal alkoxide, such as sodium ethoxide or potassium tert-butoxide. Organic lithium compounds, such as BuLi or lithium diisopropylamide (LDA), are also suitable for generating carbanions.

The inert solvent comprises aprotic solvent, protic solvent or their mixture.

In another aspect of the invention, a second process for preparing azelaic acid is disclosed in scheme 2 as shown in FIG. 2. The process comprises following steps. The steps include: react a carbanion with a compound has a formula of (1) to form a first intermediate having a formula of (3), react dialkyl malonate or meldrum's acid with the first intermediate to form a second intermediate (4) or (5), perform alcoholysis of the second intermediate (4) or (5) to form a alkyl tri-ester (6), hydrolyze the alkyl tri-ester in the presence of a base to obtain a salt, acidify the salt to a tri-acid, and decarboxylate the tri-acid in presence of acids to obtain azelaic acid. The azelaic acid prepared according to the process does not contain fatty acids, such as pelargonic acid.

In one embodiment, the carbanions are generated by adding a deprotonating reagent to a compound has alpha hydrogen atoms adjacent to nitrile groups in inert solvents.

The compound has alpha hydrogen atoms adjacent to nitrile groups comprises acetonitrile, cyanoacetic acid, alkyl cyanoacetate or malonitrile.

The de-proton reagent comprises strong bases or weak bases.

The strong bases comprise metal amide, such as sodium amide or potassium amide, or metal alkoxide, such as sodium ethoxide or potassium tert-butoxide. Organic lithium compounds, such as BuLi or LDA, are also suitable for generating carbanions.

The inert solvent comprises aprotic solvent, protic solvent or their mixture.

The acids for decarboxylation of the tri-acid are strong acids that comprise H2SO4, HCl(aq), HBr(aq), methanesulfonic acid, trifluoroacetic acid, or strong solid acid, such as Nafion-H or Amberlyst-15.

In still another aspect of the invention, a third process for preparing azelaic acid is disclosed.

The process for preparing azelaic acid comprises following steps.

Step i: React a compound has alpha-protons with a pentane has two leaving groups bound to 1 and 5 carbon in the presence of a base to form a 1,7 tetra-substituted heptane as shown in formula (A).

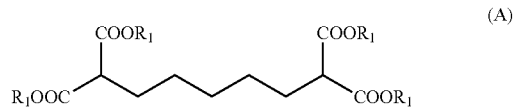

$R_1$ is selected from the group consisting of methyl, ethyl, propyl, butyl, allyl, phenyl and benzyl.

Step ii: Hydrolyze the 1,7 tetra-substituted heptane to form a salt of tetra-carboxylic acid as shown in formula (B).

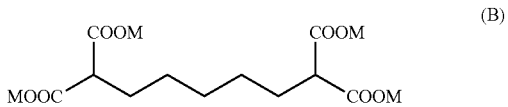

M is Li, Na or K.

Step iii: Neutralize the salt of tetra-carboxylic acid to get the tetra-carboxylic acid. Preferable, the tetra-carboxylic acid is purified by recrystallization.

Step iv: Perform decarboxylation of the tetra-carboxylic acid in the presence of a organic sulfonic acid to form azelaic acid. The azelaic acid prepared according to the process does not contain fatty acid impurities, such as pelargonic acid.

In one embodiment, the compound has alpha-protons is diethyl malonate.

In one embodiment, the pentane has two leaving groups bound to 1 and 5 carbon comprises 1,5 di-halopentane or 1,5 di-sulfonate pentane.

In one embodiment, the base comprises an alkali metal carbonate, alkali metal alkoxide or alkali metal amide.

In one embodiment, the decarboxylation of the tetra-carboxylic acid is performed between 100 and 150° C.

In one embodiment, the organic sulfonic acid comprises methanesulfonic acid, p-toluenesulfonic acid, benzenesulfonic acid or perfluorosulfonic acid.

In still another aspect of the invention, a fourth process for preparing azelaic acid is disclosed.

The process for preparing azelaic acid comprises following steps.

Step i: react a compound has alpha-protons with a pentane has two leaving groups bound to 1 and 5 carbon in the presence of a base to form a 1,7 tetra-substituted heptane as shown in formula (C).

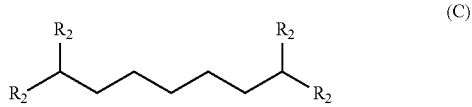

(C)

$R_2$ is nitrile (—CN) or tert-butyl ester.

Step ii: hydrolyze the 1,7 tetra-substituted heptane in acidic condition to form a tetra-carboxylic acid as shown in formula (D). Preferable, the tetra-carboxylic acid is purified by recrystallization.

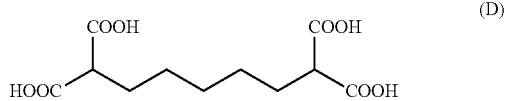 [SMILES: O=C(O)C(CCCCCC(C(=O)O)C(=O)O)C(=O)O]

(D)

Step iii: perform decarboxylation of the tetra-carboxylic acid in the presence of a organic sulfonic acid to form azelaic acid. The azelaic acid prepared according to the process does not contain fatty acid impurities, such as pelargonic acid.

In one embodiment, the compound has alpha-protons is di-tert butyl malonate or malonontrile.

In one embodiment, the pentane has two leaving groups bound to 1 and 5 carbon comprises 1,5 di-halopentane or 1,5 di-sulfonate pentane.

In one embodiment, the base comprises an alkali metal carbonate, alkali metal alkoxide or alkali metal amide.

In one embodiment, the decarboxylation of the tetra-carboxylic acid is performed between 100 and 150° C.

In one embodiment, the organic sulfonic acid comprises methanesulfonic acid, p-toluenesulfonic acid, benzenesulfonic acid or perfluorosulfonic acid.

Accordingly, the present invention provides (1) a more safe process for preparing azelaic acid without using ozone cleavage oxidation; (2) a scalable process for preparing azelaic acid through an isolated intermediate, the tetra-carboxylic acid; and (3) a suitable process for preparing pharmaceutical grade azelaic acid with controlled impurity profile.

BRIEF DESCRIPTION OF THE PREFERRED EMBODIMENTS

Figure 1:
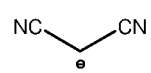
FIG. 1 is a reaction scheme of the first process for preparing azelaic acid.
Figure 1:
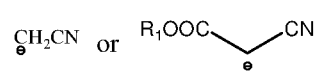
Figure 1:
Figure 1:
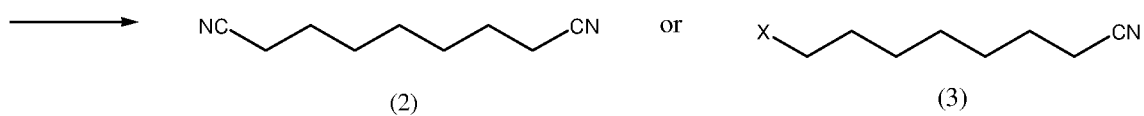
Figure 1:
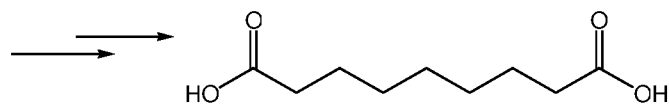

In a first embodiment, the first process for preparing azelaic acid is disclosed in scheme 1 as shown in FIG. 1. The first process comprises following steps. The steps include: react a carbanion with a compound has a formula of (1) to form an intermediate having formula of (2). Perform alcoholysis of the intermediate to form an alkyl di-ester; and hydrolyze the alkyl di-ester in the presence of bases to obtain a alkyl di-acid salt; and follow by acidifying the alkyl di-acid salt to obtain azelaic acid; or hydrolyze the alkyl di-ester in the presence of acids to obtain azelaic acid. The azelaic acid prepared according to the process does not contain fatty acid impurities, such as pelargonic acid.

The compound has a formula of (1) comprises a pentane has two leaving groups bound to 1 and 5 carbon.

In one example of the first embodiment, the carbanions are generated by adding a deprotonating reagent to a compound has alpha hydrogen atoms adjacent to nitrile groups or electron-withdrawing groups in inert solvents.

The compound has alpha hydrogen atoms adjacent to nitrile groups comprises acetonitrile, cyanoacetic acid, alkyl cyanoacetate or malonitrile.

The compound has alpha hydrogen atoms adjacent to electron-withdrawing groups comprises diethyl malonate or di tert butyl malonate.

The deprotonating reagent comprises strong bases or weak bases.

The strong bases comprise metal amide, such as sodium amide or potassium amide, or metal alkoxide, such as sodium ethoxide or potassium tert-butoxide. Organic lithium compounds, such as BuLi or lithium diisopropylamide (LDA), are also suitable for generating carbanions.

The inert solvent comprises aprotic solvent, protic solvent or their mixture.

Figure 2:
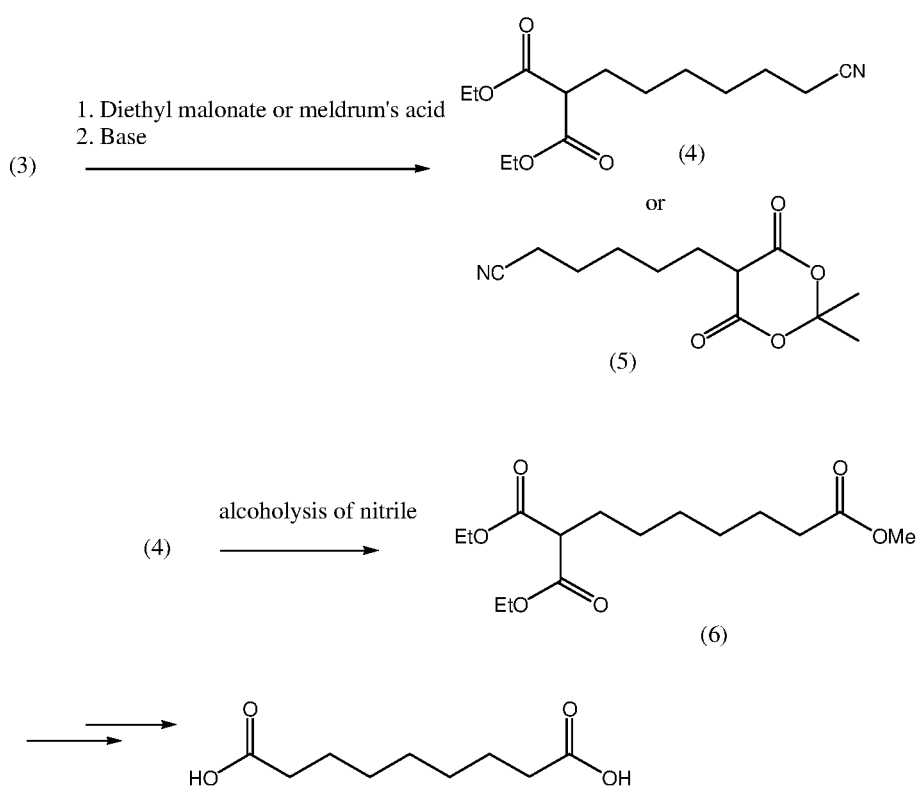
FIG. 2 is a reaction scheme of the second process for preparing azelaic acid.

In a second embodiment, the second process for preparing azelaic acid is disclosed in scheme 2 as shown in FIG. 2. The second process comprises following steps. The steps include: react a carbanion with a compound has a formula of (1) to form a first intermediate having formula of (3), react dialkyl malonate or meldrum's acid with the first intermediate to form a second intermediate (4) or (5), alcoholysis of the second intermediate (4) or (5) to a alkyl tri-ester (6), hydrolyze the alkyl tri-ester in the presence of a base to obtain a salt, acidify the salt to a tri-acid, and decarboxylate the tri-acid in presence of acids to obtain azelaic acid. The azelaic acid prepared according to the process does not contain fatty acid impurities, such as pelargonic acid.

In one example of the second embodiment, the carbanions are generated by adding a deprotonating reagent to a compound has alpha hydrogen atoms adjacent to nitrile groups in inert solvents.

The compound has alpha hydrogen atoms adjacent to nitrile groups comprises acetonitrile, cyanoacetic acid, alkyl cyanoacetate or malonitrile.

The de-proton reagent comprises strong bases or weak bases.

The strong bases comprise metal amide, such as sodium amide or potassium amide, or metal alkoxide, such as sodium ethoxide or potassium tert-butoxide. Organic lithium compounds, such as BuLi or LDA, are also suitable for generating carbanions.

The inert solvent comprises aprotic solvent, protic solvent or their mixture.

The acids for decarboxylation of the tri-acid are strong acids that comprise H2SO4, HCl(aq), HBr(aq), methanesulfonic acid, trifluoroacetic acid, or strong solid acid, such as Nafion-H or Amberlyst-15.

In a third embodiment, a third process for preparing azelaic acid is disclosed.

The third process for preparing azelaic acid comprises following steps.

Step i: React a compound has alpha-protons with a pentane has two leaving groups bound to 1 and 5 carbon in the presence of a base to form a 1,7 tetra-substituted heptane as shown in formula (A).

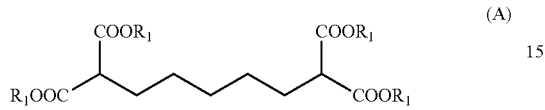

(A)

$R_1$ is selected from the group consisting of methyl, ethyl, propyl, butyl, allyl, phenyl and benzyl.

Step ii: Hydrolyze the 1,7 tetra-substituted heptane to form a salt of tetra-carboxylic acid as shown in formula (B).

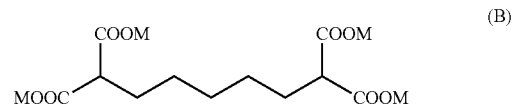

(B)

M is Li, Na or K.

Step iii: Neutralize the salt of tetra-carboxylic acid to get the tetra-carboxylic acid. Preferable, the tetra-carboxylic acid is purified by recrystallization.

Step iv: Perform decarboxylation of the tetra-carboxylic acid in the presence of a organic sulfonic acid to form azelaic acid. The azelaic acid prepared according to the process does not contain fatty acid impurities, such as pelargonic acid.

In one example of the third embodiment, the compound has alpha-protons is diethyl malonate.

In one example of the third embodiment, the pentane has two leaving groups bound to 1 and 5 carbon comprises 1,5 di-halopentane or 1,5 di-sulfonate pentane. Preferably, the 1,5 di-halopentane is 1,5 di-bromopentane.

In one example of the third embodiment, the base comprises an alkali metal carbonate, alkali metal alkoxide or alkali metal amide.

Preferably, the alkali metal alkoxide comprises sodium methoxide, sodium ethoxide, or potassium tert-butoxide.

In one example of the third embodiment, the decarboxylation of the tetra-carboxylic acid is performed between 100 and 150° C.

In one example of the third embodiment, the organic sulfonic acid comprises methanesulfonic acid, p-toluenesulfonic acid, benzenesulfonic acid or perfluorosulfonic acid.

In a fourth embodiment, a fourth process for preparing azelaic acid is disclosed.

The fourth process for preparing azelaic acid comprises following steps.

Step i: react a compound has alpha-protons with a pentane has two leaving groups bound to 1 and 5 carbon in the presence of a base to form a 1,7 tetra-substituted heptane as shown in formula (C).

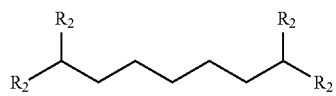

(C)

$R_2$ is nitrile (—CN) or tert-butyl ester.

Step ii: hydrolyze the 1,7 tetra-substituted heptane in acidic condition to form a tetra-carboxylic acid as shown in formula (D). Preferable, the tetra-carboxylic acid is purified by recrystallization.

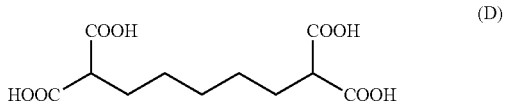 [SMILES: O=C(O)C(CCCCCC(C(=O)O)C(=O)O)C(=O)O]

(D)

Step iii: perform decarboxylation of the tetra-carboxylic acid in the presence of a organic sulfonic acid to form azelaic acid. The azelaic acid prepared according to the process does not contain fatty acid impurities, such as pelargonic acid.

In one example of the fourth embodiment, the compound has alpha-protons is di-tert butyl malonate or malonontrile.

In one example of the fourth embodiment, the pentane has two leaving groups bound to 1 and 5 carbon comprises 1,5 di-halopentane or 1,5 di-sulfonate pentane. Preferably, the 1,5 di-halopentane is 1,5 di-bromopentane.

In one example of the fourth embodiment, the base comprises a alkali metal carbonate, alkali metal alkoxide or alkali metal amide.

Preferably, the alkali metal alkoxide comprises sodium methoxide, sodium ethoxide, or potassium tert-butoxide.

In one example of the fourth embodiment, the decarboxylation of the tetra-carboxylic acid is performed between 100 and 150° C.

In one example of the fourth embodiment, the organic sulfonic acid comprises methanesulfonic acid, p-toluenesulfonic acid, benzenesulfonic acid or perfluorosulfonic acid.

Working examples of the invention are described as following paragraphs.

Example A

Reaction scheme A

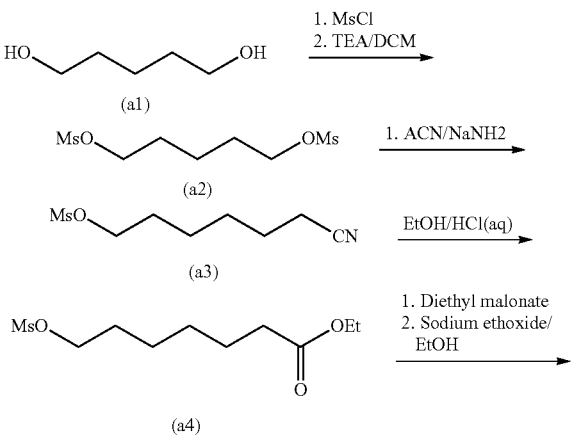

7

-continued

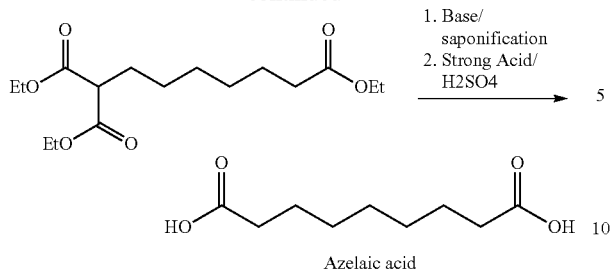

1,5-pentadiol(a1) were dissolved in TEA/DCM. Added MsCl at 0~10° C. and stirred overnight. After extraction and isolation, a di-mesylate compound (a2) was obtained. Acetonitrile(ACN) was deprotonated by NaNH2 in THF at −10~0° C. and followed by slowly adding the di-mesylate compound into the acetonitrile-NaNH2-THF mixture. After reaction, quenching and extraction, compound (a3) is obtained. Compound (a3) was treated with 6N HCl aqueous solution in EtOH to obtain compound (a4). Diethyl malonate was added to sodium ethoxide-EtOH solution and refluxed for 30 minutes, followed by adding compound (a4) to obtain a triester. The triester was hydrolyzed to a salt and use a strong acid, such as H2SO4 or Methansulfonic acid or Nafion or amberlyst-15 to acidify the salt to obtain a tri-acid and then decarboxylate the tri-acid without further neutralization and isolation to obtain azelaic acid.

Example B

Reaction Scheme B

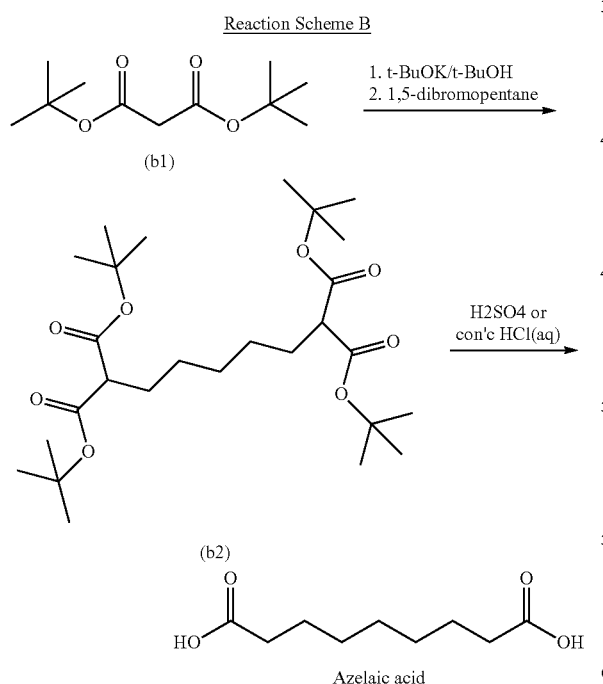

Di tert-butyl malonate was deprotonated in t-BuOK/t-BuOH and followed by adding 1,5-dibromopentane to obtain compound (b2). Compound (b2) was de-protected and decarboxylated in presence of HCl (aq) or H2SO4 or solid acid simultaneously to obtain azelaic acid.

8

Example C

Reaction scheme C

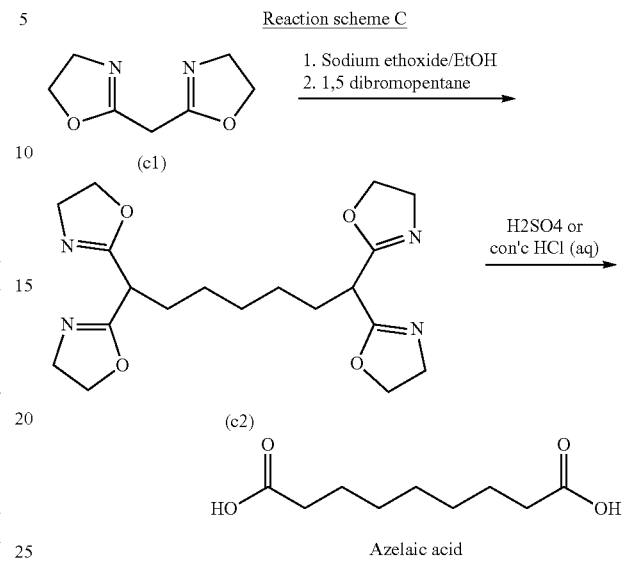

Bisoxazoline (c1) was deprotonated in sodium ethoxide/EtOH and followed by adding 1,5-dibromopentane to obtain compound (c2). Compound (c2) was de-protected and decarboxylated in presence of HCl (aq) or H2SO4 or solid acid simultaneously to obtain azelaic acid.

Example D

Reaction scheme D

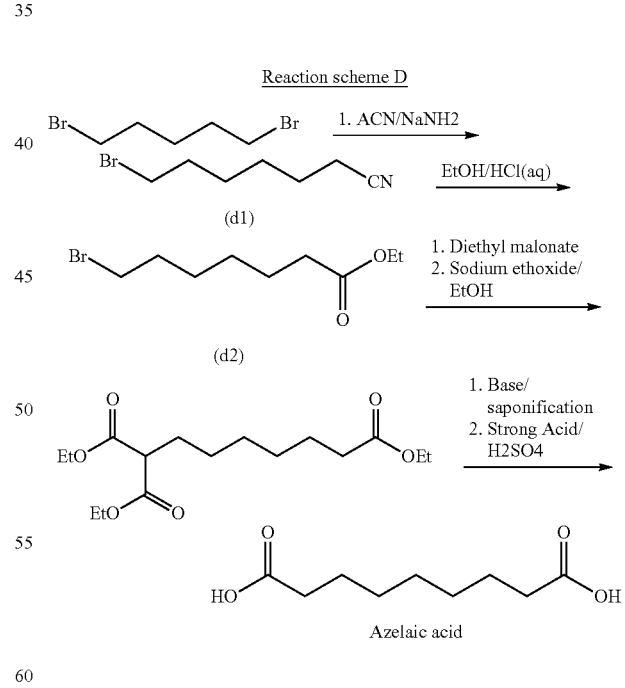

Acetonitrile(ACN) was deprotonated by NaNH2 in THF at −10~0° C. and slowly dropped 1,5-dibromopentane to obtain compound (d1). Compound (d1) was treat 6N HCl aqueous solution in EtOH to obtain compound (d2). Diethyl malonate was added to sodium ethoxide-EtOH solution and refluxed for 30 minutes, followed by adding compound (d2) to obtain a triester. The triester was hydrolyzed to a salt and use a strong acid, such as H2SO4 or Methansulfonic acid or Nafion or amberlyst-15 to acidify the salt to obtain a tri-acid and then decarboxylate the tri-acid without further neutralization and isolation to obtain azelaic acid.

Example E: Preparation of 1,7 Tetra-Substituted Heptane

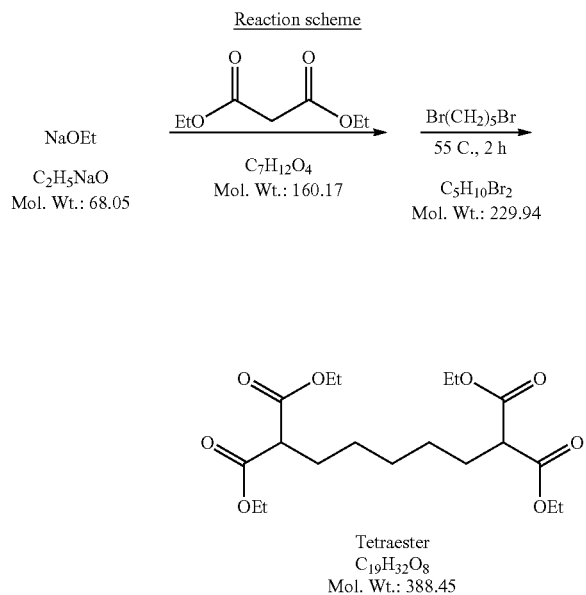

Sodium ethoxide solution (42 g; 21 wt. % in Ethanol) was charged into a 250 mL-3 neck reactor with N2 flow. The content was heated to 40±5° C. and then Diethylmalonate (42 g) was slow charged into with vigorously stir. The mixture was stirred for another 20 min. 1,5-dibromopentane (10 g) was slow charged into and the mixture was stirred at 55±5° C. for 2 h. The reactant was quenched under 20° C. with 2N HCl(aq). The upper organic layer was set aside and the lower aqueous layer was extracted with Toluene. The organic layers were combined and washed with 10% NaCl (aq) twice. After distilling out toluene, a tetraester ($C_{19}H_{32}O_8$) solution was gained.

Example F: Preparation of 1,7 Tetra-Substituted Heptane

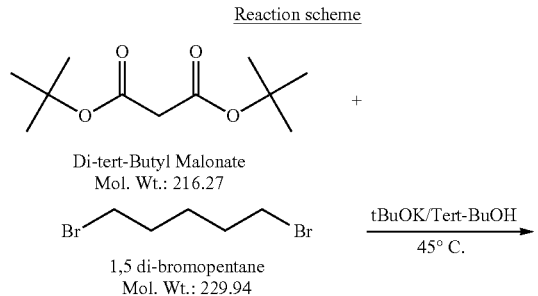

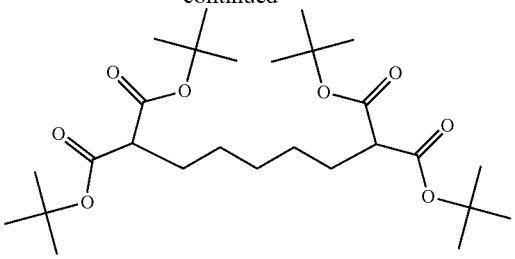

Tetra-ester
Mol. Wt.: 500.67

3.77 g of Di-tert-butyl malonate (DTBM) is dissolved in tert-butanol (25 g). The 1.96 g of tBuOK and 2 g of 1,5-dibromopentane are added to the mixture then heat the reaction to 45° C. 0.32 g of tBuOK is added slowly to the reaction at 45° C. then keeps stirring for 1 hour. Repeat this step twice and the reaction is stirred at 45° C. until the HPLC area % of DTBM is less than 1%. Add 14 g of 10% Acetic acid to remove the tBuOK and add 20 g of MTBE to extract the tetraester. Collect the organic layer and add fresh MTBE (20 g) to extract the tetraester again. Combine two MTBE layers and add 30 g of water to wash the MTBE layer. Add 30 g of 5% NaHCO3(aq) to wash the MTBE layer then add 30 g of water to wash the MTBE layer. Add anhydrous Na2SO4 to the MTBE layer for stirring 2 hours at room temperature, filter out the Na2SO4 and get the clear MTBE filtrate. Remove MTBE by vacuum at 45° C. and get the 3.11 g of Tetra-ester. (Yield=80%). Analyze the Tetra-ester by GC.

Example G: Preparation of 1,7 Tetra-Substituted Heptane

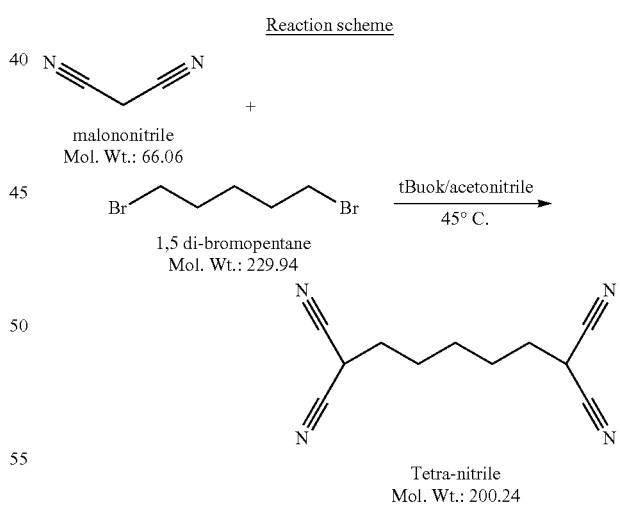

1.73 g of malononitrile (di-nitirle) is dissolved in acetonitrile (18 g). 2.94 g of tBuOK and 3 g of 1,5-dibromopentane are added to the mixture then heat the reaction to 45° C. 0.29 g of tBuOK is added slowly to the reaction at 45° C. then keeps stirring for 1 hour. Repeat this step twice and the reaction is stirred at 45° C. until the HPLC area % of malononitrile is less than 1%. Filter out the tBuOK salt and remove acetonitrile by vacuum at 30° C. and get the 3.3 g of Tetra-nitirle.

Example H: Preparation of Tetra-Carboxylic Acid

The tetraester obtained from Example E was cooled to 15±5° C. 45% NaOH(aq) was slow charged into with vigorously stirring and the content was stirred at room temperature for another 30 min. The upper organic layer was drained off and the lower aqueous layer was acidified under 20° C. with 6N HCl(aq) until pH<2. Ethyl acetate was charged into the mixture, stirred for 5 mins and then the lower aqueous layer was drained off. The upper organic layer was concentrated under vacuum. Acetone was added and stirred at room temperature for 20 mins, and then the precipitated solid was filtered off. The filtrate was concentrated under vacuum to remove two-thirds of the volume. Toluene was slowly added and the mixture was stirred at 50±2° C. for 2 h. The resultant slurry was cooled to 15±5° C. and stirred for another 30 min. The liquid was filtered off and the cake was dried under vacuum at 70±5° C. for at least 3 h and then an off-white solid was gained. MS-ESI(+): 276.

Example I: Preparation of Azelaic Acid

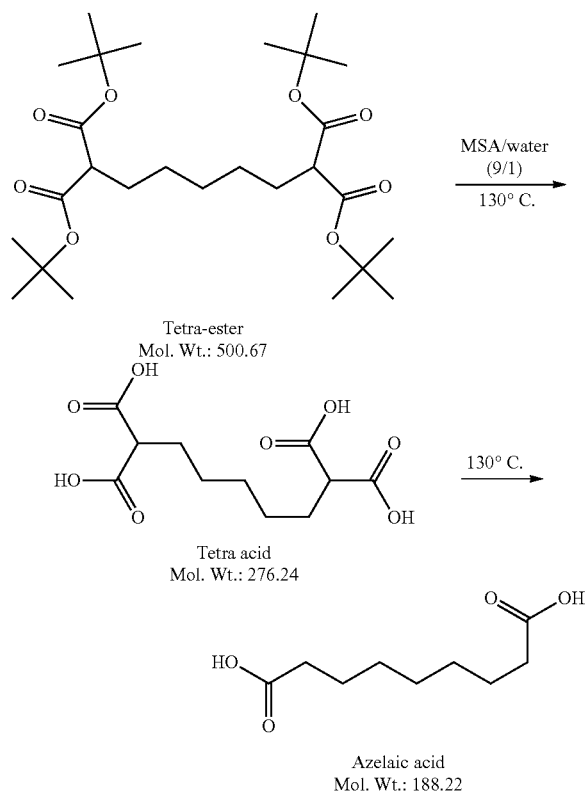

5 g of Tetra-ester is stirred with 5 g of methanesulfonic acid (MSA) solution (MSA/water: 9/1) then heat the reaction to 130° C. After the reaction reacts completely, cooling down the temperature to room temperature. Use 12N NaOH (aq) solution to adjust the pH value of the mixture to pH=9. Add Heptane to wash the mixture twice. Use 6N HCl(aq) solution to adjust the pH value of the mixture to pH5. Filter out the powder and wash the powder with heptane. The powder is dissolved in acetone, and heptane is added slowly to precipitate the azelaic acid. Repeat the aforementioned precipitating step until the area % of azelaic acid in HPLC analysis is more than 98%.

Example J: Preparation of Azelaic Acid

Reaction scheme

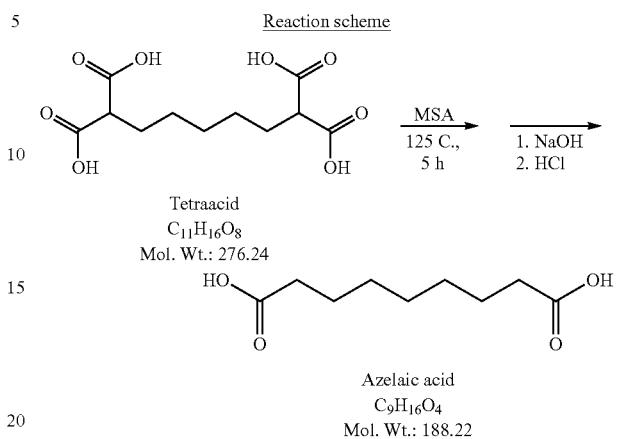

Tetraacid(1 eq) was charged into the reactor equipped with atmospheric distillation apparatus. MSA (1.5 eq) and a little water were charged into. The content was stirred at 125±5° C. for 4 h with N2 flow and water was slow charged into under 90° C. The content was neutralized under 20° C. with 15% NaOH(aq) and decolorized by activated carbon. The activated carbon was filtered off. The filtrate was acidified with 3N HCl(aq) and stirred at 15±5° C. for at least 1 hour. The solid was filtered and dried under vacuum at 70±5° C. for at least 2 h and a white solid was gained (purity>99.9%, yield~40%). MS-ESI(−): 187.

Different acids for using in decarboxylation of tetra-carboxylic acid were investigated. 6N HCl(aq) only get about 5% of azelaic acid after reaction 4 hours at 105° C.. However, the decarboxylation of tetra-carboxylic acid runs smoothly in the presence of a organic sulfonic acid aqueous solution. Therefore, the organic sulfonic acids are very suitable for the process.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A process for preparing azelaic acid, comprising:
   i. reacting malonontrile with a pentane having two leaving groups bound to 1 and 5 carbon in the presence of a base to form a 1,7 tetra-substituted heptane as shown in formula (C);

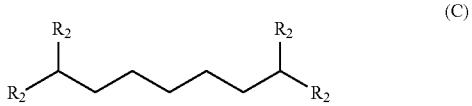

(C)

where $R_2$ is —CN;
   ii. hydrolyzing the 1,7 tetra-substituted heptane in acidic condition to form a tetra-carboxylic acid as shown in formula (D); and

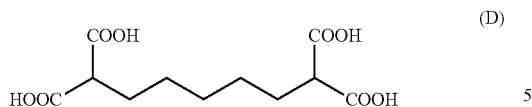

iii. performing decarboxylation of the tetra-carboxylic acid in the presence of an organic sulfonic acid to form azelaic acid.

2. The process of claim 1, wherein the pentane having two leaving groups bound to 1 and 5 carbon is selected from the group consisting of 1,5 di-halopentane and 1,5 di-sulfonate pentane.

3. The process of claim 1, wherein the base is selected from the group consisting of a alkali metal carbonate, alkali metal alkoxide and alkali metal amide.

4. The process of claim 3, wherein the alkali metal alkoxide is selected from the group consisting of sodium methoxide, sodium ethoxide, and potassium tert-butoxide.

5. The process of claim 1, wherein the decarboxylation of the tetra-carboxylic acid is performed at a temperature between 100 and 150° C..

6. The process of claim 1, wherein the organic sulfonic acid is selected from the group consisting of methanesulfonic acid, p-toluenesulfonic acid, benzenesulfonic acid and perfluorosulfonic acid.

* * * * *